United States Patent
Schütz

(10) Patent No.: US 7,500,584 B2
(45) Date of Patent: Mar. 10, 2009

(54) MOUTH RINSING DEVICE HAVING TWO DETACHABLY CONNECTABLE HOUSINGS

(75) Inventor: Alfred Schütz, Zollikofen (CH)

(73) Assignee: Gimelli Produktions AG, Zollikofen (CH)

( * ) Notice: Subject to any disclaimer, the term of this patent is extended or adjusted under 35 U.S.C. 154(b) by 423 days.

(21) Appl. No.: 11/176,310

(22) Filed: Jul. 8, 2005

(65) Prior Publication Data
US 2006/0008373 A1    Jan. 12, 2006

(30) Foreign Application Priority Data
Jul. 8, 2004    (DE)    ............... 10 2004 032 976

(51) Int. Cl.
*B67D 5/60*    (2006.01)
(52) U.S. Cl. .............. 222/464.5; 222/325; 222/382; 15/22.1
(58) Field of Classification Search ... 222/464.1–464.5, 222/8, 211, 285, 325, 382, 523; 15/22.1, 15/315, 433
See application file for complete search history.

(56) References Cited

U.S. PATENT DOCUMENTS

| | | | | |
|---|---|---|---|---|
| 1,296,742 A | * | 3/1919 | Bevington | 220/8 |
| 2,584,167 A | * | 2/1952 | Sundholm | 222/88 |
| 3,006,506 A | * | 10/1961 | Germano | 222/49 |
| 3,144,867 A | * | 8/1964 | Trupp et al. | 433/88 |
| 3,430,654 A | * | 3/1969 | Mills | 137/625.28 |
| 3,674,179 A | * | 7/1972 | Galloway | 222/94 |
| 4,068,974 A | * | 1/1978 | Meyer et al. | 401/150 |
| 4,470,526 A | * | 9/1984 | Cha et al. | 222/320 |
| 4,801,049 A | * | 1/1989 | Thompson | 222/179.5 |
| 5,746,350 A | * | 5/1998 | Nishigami et al. | 222/95 |
| 5,799,834 A | * | 9/1998 | Small et al. | 222/148 |
| 5,921,441 A | * | 7/1999 | Small et al. | 222/148 |
| 5,980,489 A | * | 11/1999 | Kriesel | 604/131 |
| 6,227,412 B1 | * | 5/2001 | Sweeton | 222/189.1 |
| 6,622,892 B2 | * | 9/2003 | Vance | 222/143 |
| 6,669,390 B1 | * | 12/2003 | Porter et al. | 401/186 |
| 6,827,243 B1 | * | 12/2004 | Nuzzolese | 222/628 |

(Continued)

FOREIGN PATENT DOCUMENTS

DE    195 25 738 A1    2/1996
DE    296 19 987 U1    6/1997

OTHER PUBLICATIONS

European Search Report dated Oct. 4, 2005 w/English Translation (six (6) pages).

*Primary Examiner*—Kevin P Shaver
*Assistant Examiner*—Andrew P Bainbridge
(74) *Attorney, Agent, or Firm*—Crowell & Moring LLP

(57) ABSTRACT

A mouth rinsing device comprising a pump housing and a reservoir. These two housings are arranged in series; i.e., the reservoir is attached to the base of the pump housing. A riser tube having a head on its end is situated on the pump housing and is fixed there by means of a lock so that only the head protrudes. When the reservoir is attached the lock is simultaneously released, so that the riser tube is able to slide into the reservoir and the intake opening is situated just above the base. After the reservoir is removed, the riser tube may be pushed in again manually. The riser tube is subsequently fixed in the retracted position by locking the head to the base of the pump housing.

13 Claims, 3 Drawing Sheets

U.S. PATENT DOCUMENTS

| | | | |
|---|---|---|---|
| 6,957,925 B1* | 10/2005 | Jacobs et al. | 401/270 |
| 7,080,980 B2* | 7/2006 | Klupt | 433/80 |
| 2001/0003342 A1* | 6/2001 | Faughnder et al. | 222/211 |
| 2002/0121519 A1* | 9/2002 | Martin et al. | 220/296 |
| 2002/0197174 A1* | 12/2002 | Howard | 417/417 |
| 2003/0221270 A1* | 12/2003 | Kuo | 15/29 |
| 2004/0144884 A1* | 7/2004 | He et al. | 242/599 |
| 2005/0006407 A1* | 1/2005 | Lawson et al. | 222/153.13 |

* cited by examiner

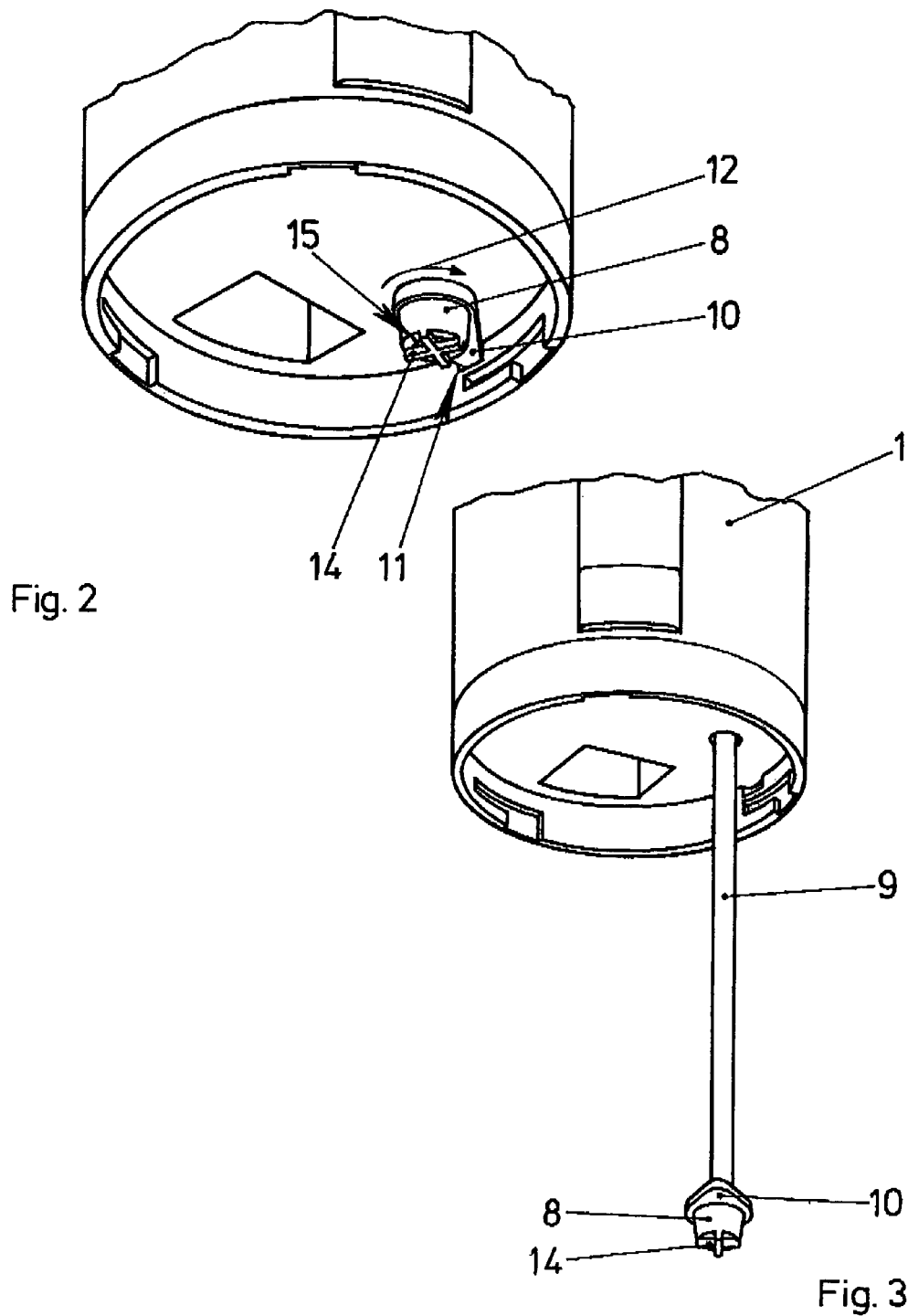

MOUTH RINSING DEVICE HAVING TWO DETACHABLY CONNECTABLE HOUSINGS

BACKGROUND OF THE INVENTION

This invention relates to a mouth rinsing device and, more particularly, this invention relates to a mouth rising device having two detachably connectable housings, the first housing being a pump housing having in its interior at least one pump and a water outlet nozzle on the upper end, and the second housing forming a water reservoir and the pump being connected to a riser tube terminating above the base of the reservoir.

Such a mouth rinsing device is known from DE 195 25 738, for example: a water outlet nozzle is located at the upper end of a slender pump housing, below which a pump is situated in the pump housing, and further below an electric motor for driving the pump, and, lastly, at the base of the pump housing, a battery for supplying power to the pump. Next to the pump housing is located a second housing which forms a water reservoir and which extends practically over the entire length of the pump housing and is detachably connected thereto. A riser tube extends from the underside of a bay on the upper end of the pump housing down to the base of the reservoir. This arrangement has two disadvantages. On the one hand, the parallel configuration of pump housing and reservoir results in a relatively thick structure that is difficult to grasp. On the other hand, the riser tube may be damaged when the water reservoir is replaced, since the riser tube must be laboriously threaded into the reservoir.

SUMMARY OF THE INVENTION

An object of the present invention, therefore, is to provide a mouth rinsing device that is easy to hold and for which the reservoir can be replaced without problems.

The object is achieved according to the invention by the fact that the water reservoir is detachably fastened to the underside of the pump housing, that the riser tube can be removed from the pump housing, and that the end of the riser tube has a head which is detachably fixed to the underside of the pump housing by means of a latch, an actuating element for the latch being located on the water reservoir in such a way that the latch is released when the reservoir is attached to the pump housing.

The arrangement of the pump housing and reservoir in series results in an overall slender housing for the mouth rinsing device which is relatively easy to grasp, even for small hands. There is no risk of damage to the riser tube, since it is inserted first into the pump housing and is automatically released only after the reservoir is fastened to the underside of the pump housing, thus being introduced into the reservoir until the head with the intake opening is near the base of the reservoir.

In order to slide the riser tube into the reservoir, it is provided that the riser tube comprises a stable pipe having a length at least equal to the height of the reservoir, and that a pipe guide is present in the pump housing. The tube automatically slides from this guide relatively easily under the action of gravitational force or a spring, but may also be easily pushed in again manually as soon as the reservoir has been detached from the pump housing.

One easily handled connection of the reservoir to the pump housing is represented by a twist lock, which preferably is composed of at least two bayonet locks. Such a connection is easily managed and does not require complicated instructions.

To hold the head at the underside of the pump housing, it is provided that the latch is fastened to the head and cooperates with an undercut at the base of the pump housing.

The base of the pump housing preferably has a circumferential edge in the shape of a ridge, which in the immediate vicinity of the head has a grooved indentation extending in the circumferential direction. The latch also has a flat clip, projecting from the head, which engages with the indentation when the head is rotated such that the clip is oriented toward the edge.

The circumferential ridge also serves as a carrier for multiple slots for the bayonet lock which are situated inside the ridge and which cooperate with corresponding, outwardly projecting slot pins. Both locks are preferably positioned at regular intervals on the circumference of the reservoir or pump housing, so that a particular alignment of the two parts is not necessary during installation. As a result, however, an appropriate number of actuating elements must be present on the reservoir so that one of the actuating elements cooperates with the latch for the head, regardless of the angular position between the pump housing and the reservoir.

In the simplest case, the actuating elements comprise open-edge recesses in the edge of the reservoir. One of these recesses engages with the clip which forms the latch, and takes the clip along with it when the reservoir is rotated relative to the pump housing in order to close the bayonet locks.

The head is provided with spacers on its underside, the intake opening for the riser tube being situated above the spacers. This ensures that the intake openings cannot become blocked by resting at the base of the reservoir.

The spacers also form a stop catch at the base of the reservoir which allows the riser tube to be loaded with a spring which acts in the direction of extension. The spring ensures that the intake opening is always located near the base of the reservoir, regardless of the angular tilt of the housing.

To provide the largest possible reservoir which can be reduced in size for transport purposes, the reservoir may have a telescopically extendable design which allows it to be collapsed to a smaller height when not in use.

As a rule, this also makes it necessary to provide the riser tube with a telescopically extendable design.

Other objects, advantages and novel features of the present invention will become apparent from the following detailed description of the invention when considered in conjunction with the accompanying drawings.

BRIEF DESCRIPTION OF THE DRAWINGS

FIG. 2 shows an additional illustration of the underside of the pump housing with a retracted riser tube;

FIG. 3 shows the pump housing with an extended riser tube;

Figure 1:
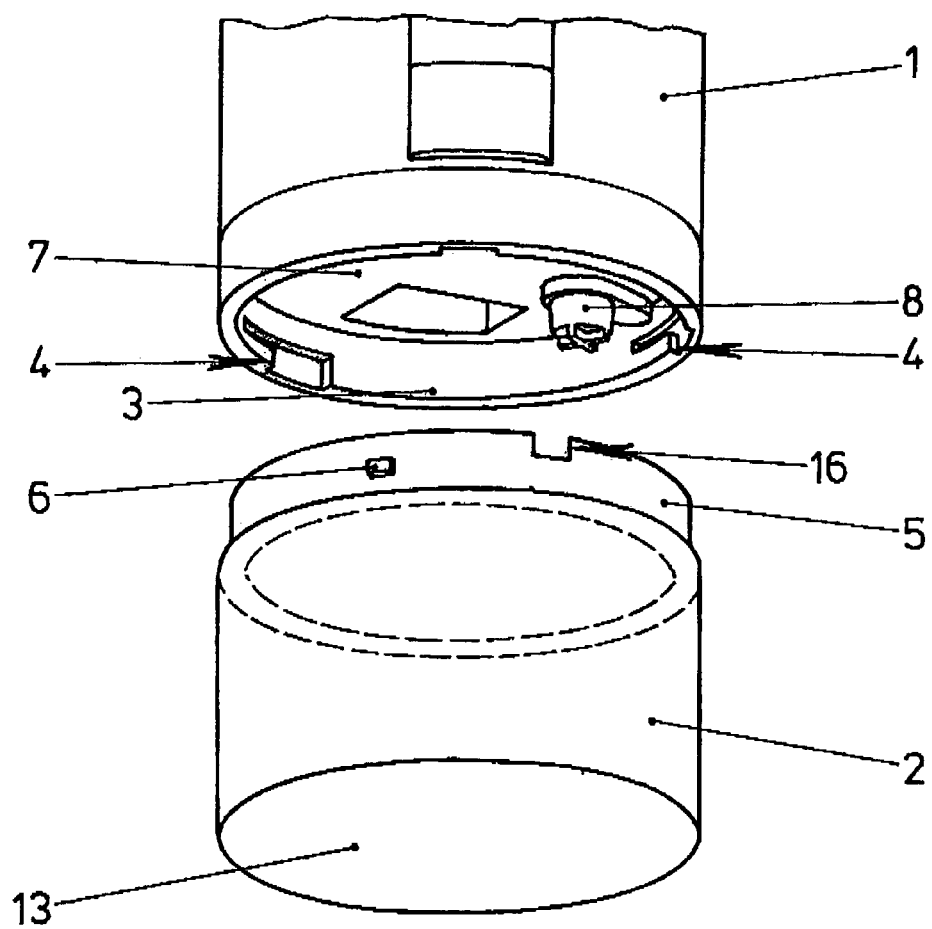
FIG. 1 shows a perspective view of the lower end of the pump housing, i.e., the upper edge of the reservoir.

Reference is first made to FIG. 1.

DETAILED DESCRIPTION OF THE PREFERRED EMBODIMENTS

The upper half of FIG. 1 shows the lower part of a cylindrical pump housing 1. An electric motor pump and batteries, or rechargeable batteries (not illustrated here in greater detail) for driving the motor are located in the pump housing 1. A likewise cylindrical water reservoir 2 having the same external diameter is located on the underside, so that the two housings fit flush into one another and form a housing for a mouth rinsing device having a continuous cylindrical shape.

For connecting the pump housing 1 to the reservoir 2 the pump housing 1 has a circumferential ridge 3, on the inside of which are located three slots 4 for bayonet locks.

The upper edge 5 of the reservoir 2 is inwardly recessed in a step-like manner so as to allow insertion into the opening formed by the ridge 3. On the exterior of the edge 5 slot pins 6 are located which are inserted into the slots 4, whereby a rotation of the reservoir 2 about its longitudinal axis introduces the slot pins 6 into the circumferentially running section of the slots 4.

At the base 7 of the pump housing 1 is located the head 8 of a riser tube 9 which, as shown in FIG. 3, can be removed from the pump housing.

The riser tube 9 comprises a stable pipe which is led into a corresponding guide (not illustrated in greater detail here) in the pump housing 1, so that the riser tube 9 can be retracted and extended in the axial direction.

To enable the riser tube 9 to be fixed in the retracted position, the head 8 has a laterally projecting clip 10 which functions as a latch and which engages with a grooved indentation 11 on the interior of the ridge 3. FIG. 2 shows the locking position of the riser tube 9: the head 8 is rotated so that the clip 10 engages with the indentation 11, thereby holding the head 8 at the base of the pump housing 1. Rotating the head 8 in the direction indicated by the arrow 12 causes the end of the clip 10 to rotate out of the indentation 11, so that now the head 8 together with the riser tube 9 is able to slide out of the guide. This occurs automatically when the reservoir 2 is placed on the pump housing 1. To this end, the edge 5 of the reservoir 2 has open-edge recesses 16, corresponding to the number of bayonet locks, one of which engages with the clip 10 when the slot pins 6 are inserted into the vertical section of the slots 4. When the reservoir 2 is rotated to lock the bayonet locks, the recess 16 takes the clip 10 along with it, thereby guiding the clip out of the indentation 11 and causing the head 8 and the riser tube to fall out of the guide.

The riser tube is long enough so that the head 8 extends to the base 13 of the reservoir 2. Spacers 14 on the underside hold the head 8 just above the base 13, thus preventing the intake opening 15 from becoming blocked by the base of the reservoir 2. A spring, not illustrated in greater detail here, holds the head 8 in this position at the base of the reservoir 2.

After the reservoir 2 has been removed, first the riser tube 9 can be manually pushed back and fixed to the base of the pump housing 1 by guiding the clip 10 into the indentation 11 by rotating the head 8. The riser tube 9 thus lies protected in the pump housing 1. When the reservoir 2 is placed back on, the lock is detached again and the riser tube 9 slides into the reservoir.

Figure 4A:
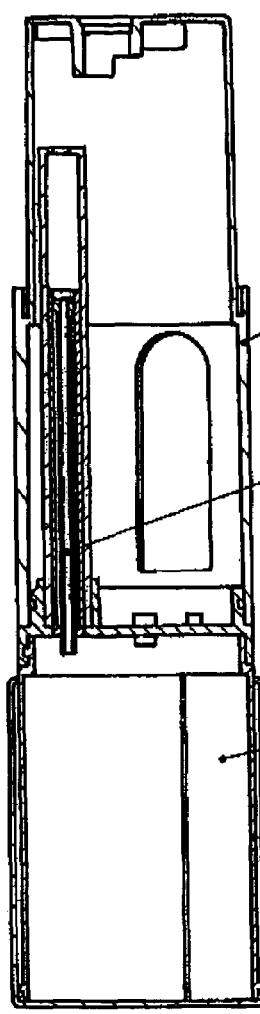
FIG. 4a shows the section through a telescopically extendable reservoir and a pump housing having a telescopically extendable riser tube, each in the retracted state.
Figure 4B:
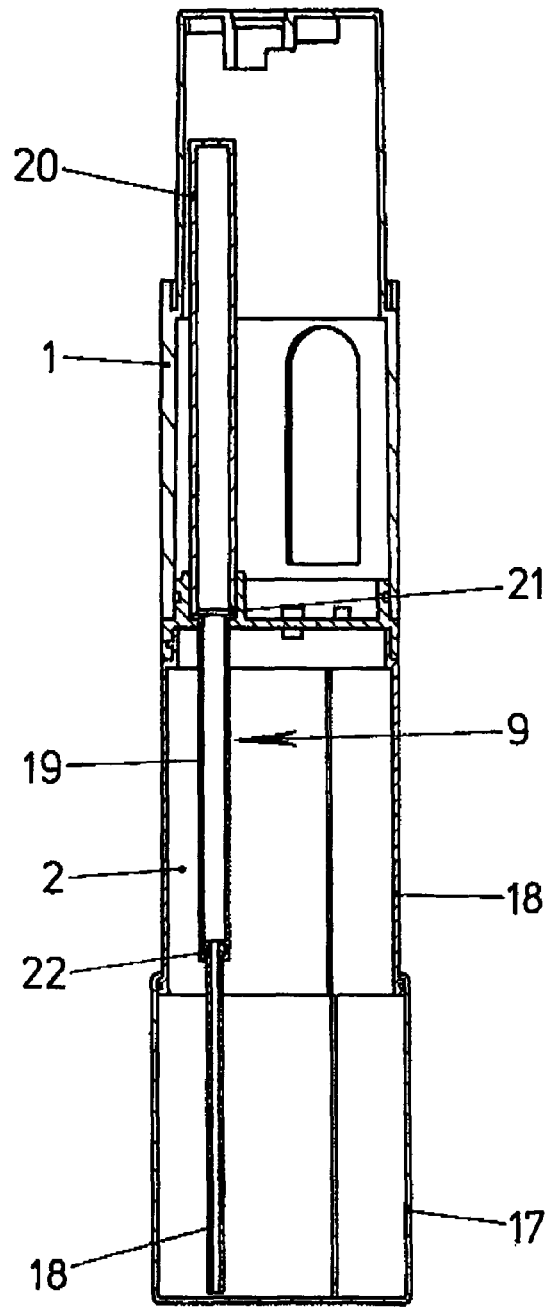
FIG. 4b shows a section corresponding to FIG. 4a, having a retracted riser tube and a collapsed reservoir.

FIGS. 4a and 4b show a combination of a pump housing 1 and a reservoir 2, the reservoir 2 comprising two parts, a base part and a sleeve part 17 and 18, respectively, which can be telescopically pushed into one another and which have approximately the same height. This allows the reservoir 2 to be collapsed to approximately half the height of its extended position (FIG. 4b) for transport purposes, as shown in FIG. 4a. The upper edge of the sleeve part 17 is similarly connected to the underside of the pump housing 1, as described above.

Since a larger and therefore higher reservoir is thus available during use, the riser tube 9 must have a correspondingly greater length in order to reach the base of the reservoir 2, and therefore cannot be housed in the pump housing 1 unless further measures are taken. Thus, the riser tube 9 must also have a telescopically extendable design, and for this purpose has an end part 18 and an intermediate part 19, which in turn is guided in a receiving sleeve 20 in the pump housing 1.

In the retracted state (see FIG. 4a), the end part 18 is situated in the intermediate part 19, which in turn is located inside the receiving sleeve 20. In the extended state (see FIG. 4b), both parts 18, 19 are respectively pulled out from the receiving sleeve 20 or the intermediate part 19 until reaching a respective stop catch 21, 22. A head 8 (not illustrated for the sake of clarity) is located at the lower free end of the end part 18, as described in greater detail above.

The invention claimed is:

1. A mouth rinsing device having two detachably connectable housings, the first housing being a pump housing having in its interior at least one pump and a water outlet nozzle on the upper end, and the second housing forming a water reservoir and the pump being connected to the reservoir via a riser tube terminating above a base of the reservoir, wherein the water reservoir is detachably fastened to the underside of a first housing part, the riser tube is selectively extendible from the pump housing, and the end of the riser tube has a head which is detachably fixed to the underside of the pump housing by means of a latch, an actuating element for the latch being located on the water reservoir in such a way that the latch is released when the reservoir is attached to the pump housing.

2. A mouth rinsing device according to claim 1, wherein the riser tube comprises a stable pipe having a length at least equal to the height of the reservoir, and a pipe guide is present in the pump housing.

3. A mouth rinsing device according to claim 1, wherein the reservoir is connected to the pump housing by means of a twist lock.

4. A mouth rinsing device according to claim 3, wherein at least two bayonet locks are provided for connecting the reservoir to the pump housing.

5. A mouth rinsing device according to claim 1, wherein the latch is fastened to the head and engages behind an undercut at the base of the pump housing.

6. A mouth rinsing device according to claim 5, wherein the base of the pump housing has a circumferential edge in the shape of a ridge, the ridge is designed as a flat clip projecting from the head, and the ridge in the immediate vicinity of the head has a grooved indentation in which the end of the clip engages when the clip is oriented toward the edge.

7. A mouth rinsing device according to claim 4, wherein the bayonet locks comprise multiple slots distributed on the interior of the ridge, and multiple outwardly projecting slot pins are present on the exterior of the reservoir.

8. A mouth rinsing device according to claim 7, wherein the bayonet locks are distributed at regular intervals on the circumference of the reservoir or pump housing, and a corresponding number of actuating elements is present on the reservoir.

9. A mouth rinsing device according to claim 8, wherein the actuating elements are formed by open-edge recesses in the edge of the reservoir.

10. A mouth rinsing device according to claim 1 further comprising spacers disposed on the underside of the head, and an intake opening is situated above the spacers.

11. A mouth rinsing device according to claim 1 wherein the reservoir has a telescopically extendable design.

12. A mouth rinsing device according to claim 11, wherein the riser tube has a telescopically extendable design.

13. A mouth rinsing device according to claim 1, wherein the riser tube has a telescopically extendable design.

* * * * *